United States Patent

Tsuchida et al.

Patent Number: 5,178,803
Date of Patent: Jan. 12, 1993

[54] METHOD OF MANUFACTURING A MULTI-LUMINAL CATHETER, AND MULTI-LUMINAL CATHETER ASSEMBLY

[75] Inventors: Kouji Tsuchida; Yoshio Ishitsu; Shigekazu Sekii, all of Fuji, Japan

[73] Assignee: Terumo Kabushiki Kaisha, Tokyo, Japan

[21] Appl. No.: 665,790

[22] Filed: Mar. 7, 1991

Related U.S. Application Data

[62] Division of Ser. No. 449,934, Dec. 18, 1989, Pat. No. 5,041,083.

[30] Foreign Application Priority Data

Jun. 25, 1987 [JP] Japan ................. 62-158114
Jun. 25, 1987 [JP] Japan ................. 62-158146

[51] Int. Cl.⁵ .............................. B29C 55/30
[52] U.S. Cl. ......................... 264/23; 264/25; 264/26; 264/296; 264/322; 264/323; 425/393
[58] Field of Search ........... 264/296, 322, 323, 23, 264/25, 26; 425/393

[56] References Cited

U.S. PATENT DOCUMENTS

| | | | |
|---|---|---|---|
| 3,545,168 | 12/1970 | Day | 264/322 |
| 4,072,146 | 2/1978 | Howes. | |
| 4,177,237 | 12/1979 | Ueno et al. | 264/296 |
| 4,263,236 | 4/1981 | Briggs et al. | |
| 4,345,963 | 8/1982 | Braber. | |
| 4,619,643 | 10/1986 | Bai. | |
| 4,670,009 | 6/1987 | Bullock. | |
| 4,682,978 | 7/1987 | Martin. | |
| 4,838,881 | 6/1989 | Bennett. | |

FOREIGN PATENT DOCUMENTS

| | | |
|---|---|---|
| 1219785 | 3/1987 | Canada. |
| 2401012 | 3/1979 | France. |
| 60-241453 | 11/1985 | Japan. |
| 60-244527 | 12/1985 | Japan. |

Primary Examiner—Jan H. Silbaugh
Assistant Examiner—Brian J. Eastley
Attorney, Agent, or Firm—Frishauf, Holtz, Goodman & Woodward

[57] ABSTRACT

A multi-luminal catheter is characterized in that the cross-sectional shape of each lumen at a connection portion for an extension tube is molded in accordance with the outer shape of the extension tube to be connected. Accordingly, smooth and hermetic connection between a catheter body and the extension tube, that has not been accomplished in the past, can be obtained, and the formation of steps of the lumen which increases fluid resistance can be prevented. This mult-luminal catheter can be produced by pressing a core metal having substantially the same shape as that of the outer shape of the extension tube into each lumen of the catheter body at the connection portion for the extension tube and inserting the connection portion for the extension tube into a molding die while heating it. Higher airtightness and connection strength can be obtained by fitting the connection end of the extension tube into each lumen at the connection portion of the multi-luminal catheter and integrating them by use of a fixing member.

14 Claims, 2 Drawing Sheets

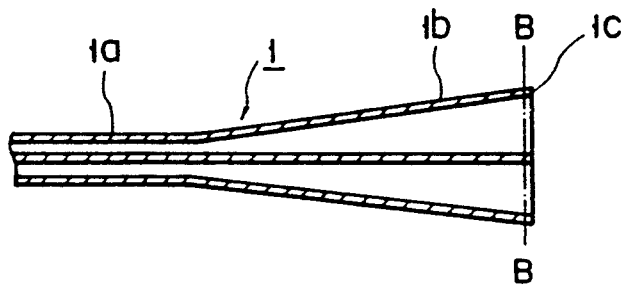
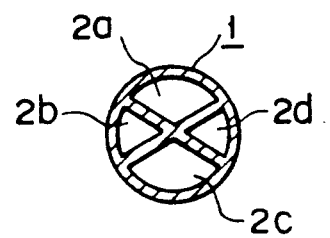
FIG. 1a  FIG. 1b
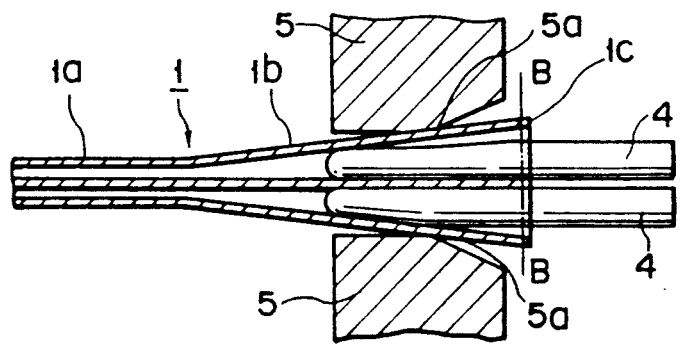
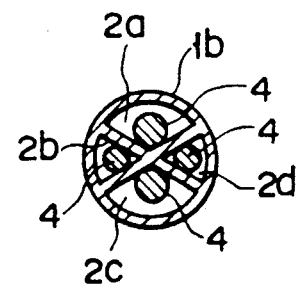
FIG. 2a  FIG. 2b
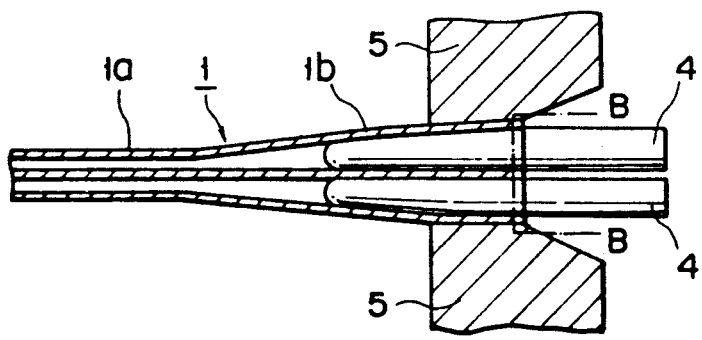
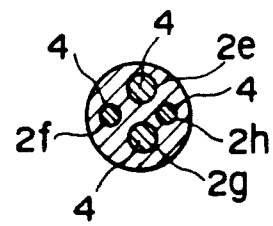
FIG. 3a  FIG. 3b

METHOD OF MANUFACTURING A MULTI-LUMINAL CATHETER, AND MULTI-LUMINAL CATHETER ASSEMBLY

This is a division of application Ser. No. 07/449,934 filed Dec. 18, 1989 U.S. Pat. No. 5,041,083.

TECHNICAL FIELD

This invention concerns a multi-luminal catheter wherein the lumens of the catheter, which have a different shape to the external form of the extension tubes to be connected to them, are given a shape which corresponds to said external form of said extension tubes at the extension tube connectors. It also concerns a method of manufacturing said catheter.

Further, this invention concerns a multi-luminal catheter assembly comprising a catheter body with multiple lumen, extension tubes connected to said catheter and members for fastening the catheter body and the extension tubes together, and a method of manufacturing said assembly.

BACKGROUND ART

In order to make most effective use of the volume of the cavities in a multi-luminal catheter, their cross-section is generally not circular, as shown in FIG. 1(b). The cross-sections of the extension tubes to be connected to the catheter body on the other hand are circular, and if these tubes are connected to the catheter without modification, airtight connections are consequently not obtained. Further, even when the cross-sections of both the catheter lumens and extension tubes are circular, the diameters of the extension tube lumens must necessarily be made smaller to insert the tubes into the catheter lumens. For this reason, a differential arises between the lumens, and gives rise to problems such as increased fluid resistance.

Conventionally, this problem was solved by making the connection through molded pieces of the same shape as the lumens, or by filling the spaces between the catheter lumens and the outer circumference of the extension tubes with adhesive.

If connections were made through molded pieces of the same shape as the catheter lumens, however, the manufacturing cost increased undesirably. If on the other hand the spaces between the inner surfaces of the catheter lumens and extension tubes were filled with adhesive, it was still difficult to obtain a perfectly airtight seal.

Further, in multi-luminal catheters manufactured by the above methods, the joint strength between the catheter body and the extension tubes is inadequate, and the tubes easily fall out of the catheter body in actual use.

This invention therefore aims to provide a multi-luminal catheter wherein extension tubes can be connected easily to the catheter body, and good air-tightness is obtained.

DISCLOSURE OF THE INVENTION

The multi-luminal catheter of this invention is characterized in that it has lumens of substantially the same shape as the ends of the extension tubes to be connected to the tube connectors of the catheter body, which consists of thermoplastic resin and has multiple lumens of different shape to the external form of said tubes.

As the shapes of the lumens at the extension tube connectors in this multi-luminal catheter, are substantially identical to the external form of said tubes, the tube connections can be made smoothly, and airtight connections can be obtained. Further, even when the cross-sections of both the catheter lumens and extension tube lumens are circular, it is possible to connect extension tubes of substantially similar diameter to the catheter lumens, and increased fluid resistance of the lumens can thus be avoided.

This invention also aims to provide a method of manufacturing said multi-luminal catheter. In this method, cores of substantially similar form the ends of the extension tube are pressed into the extension tube connectors of the catheter body, which consists of thermoplastic resin and has multiple lumens of different form to the extension tubes. The positions where the cores have been pressed into the catheter body are then heated, softened and introduced into a mold so as to create voids corresponding to the external form of the cores when the cores are subsequently withdrawn. Finally, the core insertion positions are cooled, and the cores are withdrawn.

In this method, as the multi-luminal catheter with extension tube connectors is made in such a way that the connector openings have identical shapes to the external form of the tube connecting ends, the tube connections can be made smoothly, and airtight connections can be obtained.

In molding the extension tube connector of the catheter body by said heat molding process, it is preferable if the parts to be molded are first pre-heated to the softening temperature, and then introduced into the mold while applying heat in stages.

This invention also aims to provide a multi-luminal catheter assembly comprising a multi-luminal catheter body wherein said extension tube connectors are first shaped to correspond to the external form of the ends of extension tubes, several extension tubes of which the ends are inserted into the connectors of said catheter body, and fixing members which entirely cover the connectors between said catheter body and said extension tubes, and part of the catheter body and the extension tubes near these connectors.

In this multi-luminal catheter assembly, after the catheter body and the extension tubes are connected, the connectors are fixed en bloc by covering them with a fixing member. As a result, better airtightness and joint strength are obtained than in the case where said multi-luminal catheter is used alone.

Further, this invention aims to provide a method of manufacturing said multi-luminal catheter assembly. In this method, the connecting ends of several extension tubes are inserted and fixed in the lumens of the catheter body wherein the tube connectors have been shaped to fit the external form of the tube ends, following which said catheter body, said extension tube connectors, and the part of the catheter body and part of the extension tubes near the connectors, are entirely covered with a fixing member.

In this method, said fixing member may consist only of adhesive, or it may consist of an outer casing and a filler filling the space inside the outer casing. Further, said outer casing may consist of a casing body with the form of a tube, and a cap connected to the open end of the casing.

BRIEF DESCRIPTION OF THE DRAWINGS

FIG. 1(a) is a sectional view of the base of the multi-luminal catheter;

FIG. 1(b) is a sectional view taken along the line -- in FIG. 1(a);

FIG. 2(a) is a sectional view of the molding mechanism which explains the method of manufacturing the multi-luminal catheter of this invention;

FIG. 2(b) is a sectional view taken along the line -- in FIG. 2(a);

FIG. 3(a) is a sectional view of the molding mechanism which explains the processes following FIG. 2(a);

FIG. 3(b) is a sectional view taken along the line -- in FIG. 3(a);

BEST MODE OF CARRYING OUT THE INVENTION

We shall now explain embodiment of this invention with reference to the drawings.

First, as shown in FIG. 1(a), the catheter body 1 is formed comprising a main part 1a of specified shape, and a flared base 1b with a taper for connecting extension tubes. This catheter body may be formed by any convenient method. It should however preferably be formed continuously by extrusion molding with control of resin discharge, stretching rate and internal pressure of the lumens, and then cut into desired lengths. In this way, a catheter body 1 with 4 lumens 2a-2d each having a non-circular cross-section as shown in FIG. 1b is obtained.

The thermoplastic material of catheter body 1 may be one of the conventional resins such as polyvinyl chloride, polyurethane, silicone resin and ethylene-vinyl acetate copolymer (EVA).

Figure 4:
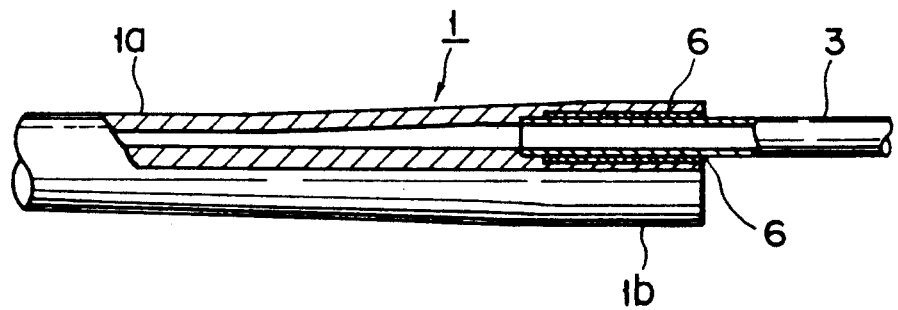
FIG. 4 is a partial sectional view showing the catheter body connected with the extension tubes.

Next, as shown in FIGS. 2a and 2b, cores 4 of substantially similar form to the extension tube 3 that is to be connected (see FIG. 4), are pressed into lumens 2a-2d to the necessary depth. Cores 4 should preferably consist of brass or stainless steel.

Subsequently, only the part of the catheter body 1 into which cores 4 have been inserted, is introduced into mold 5 and heated by hot air. The heating temperature should preferably be sufficient to slightly soften the catheter body 1. If the catheter body 1 is of polyvinyl chloride, this temperature is approx. 40°-90° C. The mold may be any of the molds normally used, but should preferably be of stainless steel if the cooling is done by means of water.

The heating carried out to raise the catheter body 1 to the softening temperature may be carried out before introducing it into mold 5, following which the catheter body 1 may be introduced into mold 5 while continuing the heating. Further, apart from hot air, the heating may be effected by a heating wire, ultrasonic waves, high frequencies or a combination of any of these methods.

The catheter body 1 is then pulled into the mold 5 while heating the part (flared base) 1b of body 1 which is to be molded. The pulling of body 1 is temporarily stopped when its end 1c is 5-20 mm in front of the entrance 5a of mold 5, and the part 1b is then heated to a higher temperature. This temperature should be high enough to fully deform the part 1b, and if the catheter body 1 is of polyvinyl chloride, for example, it should preferably be approx. 100°-150°.

When the part 1b to be molded has reached the deformation temperature, the catheter body 1 is pulled completely into mold 5, and heating is continued for a further 1-2 minutes. In this way, circular openings 2e-2h identical to the shape of cores 4 will be formed in the connecting end of catheter body 1 when the cores are removed (see FIG. 3b).

Subsequently, mold 5 is cooled by means of air or water cooling, including cooling portions of the connector portion where the cores have been inserted into the connector portion, the catheter body 1 is removed from mold 5, and cores 4 are removed from openings 2e-2h to complete the molding process.

In this way, by separating the heating of the part 1b of catheter body 1 to be molded into several stages, the optimum temperatures for pulling the body 1 in and for molding can be selected, and the molding process can proceed smoothly.

As the lumens 2e-2h of catheter body 1 molded by the above process, are identical to the external form of the extension tubes, the extension tubes can be inserted in smoothly and airtight connections can be obtained. The connection of extension tubes 3 to lumens 2e-2h of catheter body 1 can be made by pushing the tubes 3 coated with adhesive into the lumens 2e-2h, and hardening the adhesive (see FIG. 4). Examples of adhesives that can be used are epoxy adhesives, polyurethane adhesives, acrylic adhesives, EVA adhesives, silicone adhesives and phenolic adhesives, a suitable adhesive being chosen from this list. Further, apart from said adhesive method, the connection may be made by solvent welding with solvents such as ketones, esters, chlorinated carbon or aromatic hydrocarbons, by ultrasonic fusion, or by high frequency fusion.

The connection between said multi-luminal catheter and extension tubes has far superior airtightness and joint strength to conventional multi-luminal catheters, and if a fixing member is used to cover the connections between catheter body 1 and extension tubes 3, and the area near the connections, even better airtightness and joint strength can be obtained.

Figure 5:
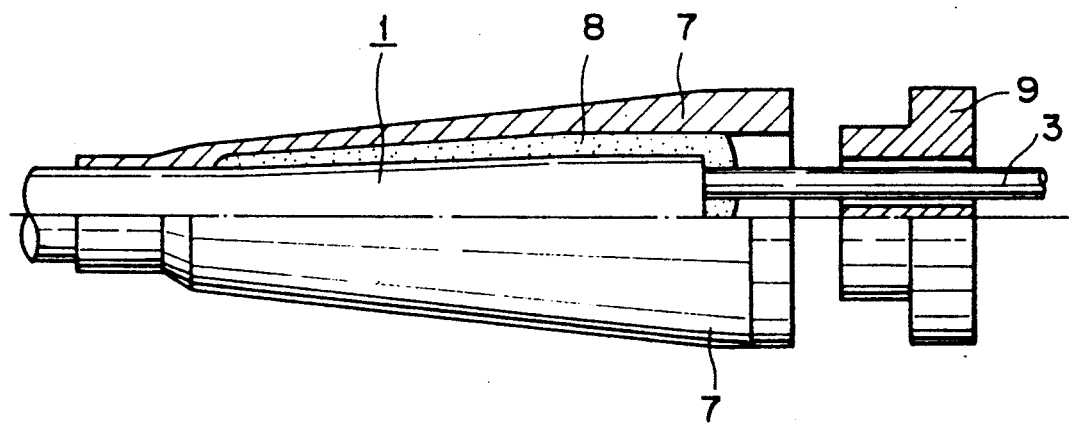
FIG. 5 is a partial sectional view showing a multi-luminal catheter in one embodiment of this invention.

FIG. 5 shows an embodiment of a multi-luminal catheter assembly using such a fixing member. As shown in FIG. 5, the area near the connector of the catheter body 1 with extension tubes 3 connected, is covered by a casing body 7 of which part has an inner diameter larger than the external diameter of the flared base 1b of catheter body 1, and the space between the casing body and the catheter body is filled with a resin 8 for filling. A cap 9 penetrated with extension tube 3 is then pushed into the open end of the casing body 7, and joined to the casing 7 by means of adhesive, ultrasonic waves or high frequency waves so as to complete the assembly. In the multi-luminal catheter assembly so obtained, the connector between the catheter body 1 and extension tubes 3, and the neighboring part of the catheter and the extension tubes are entirely covered, so the joint has improved airtightness and strength than if the catheter body 1 were used alone.

Any material may be used for the casing body 7 provided it has the required strength, suitable examples being polycarbonate, polypropylene, ABS resin and polyvinyl chloride. Further, the filler 8 used to fill the casing body 7 may be an epoxy resin, silicone resin, polyurethane resin, acrylic resin, EVA resin, phenolic resin or vinyl chloride resin.

In the above example, both casing body 7 and cap 9 are used as fixing members. In the multi-luminal catheter assembly of this invention, however, instead of this arrangement, the catheter body may for example be covered and fixed by an outer casing of one piece construction not separated into a casing body and cap, or simply by a layer of adhesive without using an outer casing.

What is claimed is:

1. A method of manufacturing a multi-luminal catheter, comprising the steps of:
   inserting cores, under pressure, in an insertion direction, into a connector portion of a catheter body of said catheter, said connector portion including at least a section thereof that is formed of a thermoplastic material, said connector portion having a plurality of lumens formed therein which respectively differ in a cross-sectional shape from a cross-sectional shape of each of a plurality of extension tubes that are insertable into said lumens, each of said cores respectively having a cross-sectional shape that substantially matches said cross-sectional shape of each of said plurality of extension tubes;
   pulling said connector portion, with said cores inserted therein, into an aperture of a mold in said insertion direction, said aperture having a diameter that is smaller than an outer diameter of said connector portion of the catheter being manufactured;
   heating said connector portion to soften at least said section thereof which is formed of said thermoplastic material as said connector portion is being pulled in said insertion direction of said cores, so as to fill a clearance between each respective core and an inner surface of a respective one of said lumens with said softened thermoplastic material so as to form an opening in said connector portion which conforms with said cross-sectional shape of the core inserted in each of said lumens;
   cooling portions of said connector portion where said cores have been inserted into said connector portion; and
   subsequently withdrawing said cores from said connector portion whereby the cross-sectional shape of a respective one of the lumens in said connector portion matches said cross sectional shape of a respective one of said extension tubes.

2. The method according to claim 1, wherein:
   said connector portion with said cores inserted therein, is first heated to a softening temperature of said catheter body, before pulling said connector portion into said aperture of said mold; and
   pulling said connector portion into said mold while applying heat in a plurality of stages.

3. The method according to claim 2, wherein:
   a plurality of parts of said catheter body of said catheter being manufactured, are first heated to said softening temperature of said catheter body before introducing said connector portion, with the cores inserted therein, into said aperture of said mold;
   partially introducing into said mold, said parts of said catheter body of said catheter being manufactured and heating said parts of said catheter body in said mold to a temperature sufficient to deform said catheter body;
   pulling substantially all of said connector portion into said mold; and
   cooling portions of said connector portion to form each of said lumens to have a cross-sectional shape that matches the cross-sectional shape of respective ones of said extension tubes.

4. The method according to claim 2, wherein:
   a plurality of parts of said catheter body of said catheter being manufactured, are first heated to said softening temperature of said catheter body after said connector portion with the cores inserted therein, has been partially pulled into said aperture of said mold;
   partially pulling into said mold, said parts of said catheter body of said catheter being manufactured and heating said parts of said catheter body in said mold to a temperature sufficient to deform said catheter body;
   pulling substantially all of said connector portion into said aperture of said mold; and
   cooling portions of said connector portion so as to form each of said lumens to have a cross-sectional shape that matches the cross-sectional shape of a respective one of said extension tubes.

5. The method according to claim 1, wherein hot air is provided to heat said connector portion.

6. The method according to claim 1, wherein a heating wire is provided to heat said connector portion.

7. The method according to claim 1, wherein ultrasonic waves are provided to heat said connector portion.

8. The method according to claim 1, wherein high frequency waves are provided to heat said connector portion.

9. The method according to claim 1, wherein heating of the connector portion is provided by at least hot air heating and heating with a heating wire.

10. The method according to claim 1, wherein heating of the connector portion is provided by at least hot air heating and ultrasonic wave heating.

11. The method according to claim 1, wherein heating of the connector portion is provided by at least hot air heating and high frequency wave heating.

12. The method according to claim 1, wherein heating of the connector portion is provided by at least heating with a heating wire and ultrasonic wave heating.

13. The method according to claim 1, wherein heating of the connector portion is provided by at least heating with a heating wire and high frequency wave heating.

14. The method according to claim 1, wherein heating of the connector portion is provided by at least ultrasonic wave heating and high frequency wave heating.

* * * * *

UNITED STATES PATENT AND TRADEMARK OFFICE
CERTIFICATE OF CORRECTION

PATENT NO. : 5,178,803
DATED : January 12, 1993
INVENTOR(S) : TSUCHIDA et al It is certified that error appears in the above-identified patent and that said Letters Patent is hereby corrected as shown below:

TITLE PAGE:

In Section [30] Foreign Application Priority Data -

Change the first Japanese application number from

"62-158114" to --62-158144--.

Signed and Sealed this

Sixteenth Day of November, 1993

Attest:

BRUCE LEHMAN

Attesting Officer        Commissioner of Patents and Trademarks